United States Patent
David et al.

(10) Patent No.: US 8,293,340 B2
(45) Date of Patent: Oct. 23, 2012

(54) PLASMA DEPOSITED MICROPOROUS ANALYTE DETECTION LAYER

(75) Inventors: Moses M. David, Woodbury, MN (US);
Neal A. Rakow, Woodbury, MN (US);
Dora M. Paolucci, St. Paul, MN (US);
John E. Trend, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 2107 days.

(21) Appl. No.: 11/275,277

(22) Filed: Dec. 21, 2005

(65) Prior Publication Data

US 2007/0141580 A1 Jun. 21, 2007

(51) Int. Cl.
*H05H 1/24* (2006.01)
*G01N 21/00* (2006.01)

(52) U.S. Cl. ......... 427/569; 422/68.1; 422/83; 977/781; 977/891

(58) Field of Classification Search .............. 422/50, 422/55, 68.1, 82.05, 83, 86–88; 427/2.11, 427/569; 977/902, 904, 920–922, 932, 953, 977/957, 958, 963, 781, 891
See application file for complete search history.

(56) References Cited

U.S. PATENT DOCUMENTS

| | | | |
|---|---|---|---|
| 4,685,940 A * | 8/1987 | Soffer et al. | 96/8 |
| 5,015,843 A | 5/1991 | Seitz et al. | |
| 5,611,998 A | 3/1997 | Aussenegg et al. | |
| 5,783,836 A | 7/1998 | Liu et al. | |
| 6,180,318 B1 | 1/2001 | Fitzer et al. | |
| 6,297,293 B1 | 10/2001 | Bell et al. | |
| 6,331,209 B1 | 12/2001 | Jang | |
| 6,396,616 B1 | 5/2002 | Fitzer et al. | |
| 6,416,938 B1 | 7/2002 | Kubacki | |
| 6,432,866 B1 | 8/2002 | Tennent et al. | |
| 7,071,287 B2 | 7/2006 | Rhine et al. | |
| 2004/0062682 A1 | 4/2004 | Rakow et al. | |
| 2004/0175957 A1 | 9/2004 | Lukas et al. | |
| 2004/0184948 A1 * | 9/2004 | Rakow et al. | 422/1 |
| 2005/0136231 A1 | 6/2005 | Voss-Kehl et al. | |
| 2005/0181198 A1 | 8/2005 | David et al. | |

FOREIGN PATENT DOCUMENTS

| | | |
|---|---|---|
| WO | WO 04/000549 A1 | 12/2003 |
| WO | WO 2005/012397 A2 | 2/2005 |
| WO | WO 2005/111588 | 11/2005 |

OTHER PUBLICATIONS

Budd et al., "Polymers of intrinsic microporosity (PIMS): robust solution-processable, organic nanoporous materials", Chem. Commun., 2004, pp. 230-231.
Product Information: DuPont® Teflon® AF amorphous fluoropolymers, 4 pages, Feb. 1998.
Rakow et al., "Optochemical Sensor and Method of Making the Same", U.S. Appl. No. 11/275,268, filed Dec. 21, 2005.
Padiyath et al., "Solar Control Multilayer Film", U.S. Appl. No. 11/313,518, filed Dec. 21, 2005.
Babu et al., "Two-step regression procedure for the optical characterization of thin films", Applied Optics, Mar. 1, 1991, vol. 30, No. 7, pp. 839-846.
McKeown et al., *Polymers of Intrinsic Microporosity (PIMS): Bridging the Void Between Microporous and Polymeric Materials*, Chemistry, A European Journal, 2005, vol. 11, pp. 2610-2620.
Budd et al., *Solution-Porcessed, Organophilic Membrane Derived from a Polymer of Intrinsic Microporosity*, Advanced Materials, Mar. 5, 2004, vol. 16, No. 5, pp. 456-459.
Budd et al., *Free Volume and Intrinsic Microporosity in Polymers*, J. Mater. Chem., 2005, vol. 15, pp. 1977-1986.
European Application No. 06845568 Supplementary Search Report dated Jan. 20, 2011.
Khomich, et al., *Hydrogenated Nanoporous Diamond Films*, Inorganic Materials, vol. 41, No. 8, 2005, pp. 812-818.
Lee, et al., *Analysis of Amorphous Carbon Thin Films by Spectroscopic Ellipsometry*, Journal of Non-Crystalline Solids, 227-230 (1998) 617-621.

* cited by examiner

*Primary Examiner* — Randy Boyer
(74) *Attorney, Agent, or Firm* — Karl G. Hanson

(57) ABSTRACT

Plasma deposited microporous analyte detection layers, method of forming analyte detection layers, and analyte sensors including the same are disclosed. An analyte sensor includes a substrate and a microporous amorphous random covalent network layer. The microporous amorphous random covalent network layer includes silicon, carbon, hydrogen and oxygen with a mean pore size in a range from 0.5 to 10 nanometers and an optical thickness in a range from 0.2 to 2 micrometers.

23 Claims, 6 Drawing Sheets

PLASMA DEPOSITED MICROPOROUS ANALYTE DETECTION LAYER

BACKGROUND

The present disclosure relates to plasma deposited microporous analyte detection layers, methods of forming analyte detection layers, and analyte sensors including the same are disclosed.

The development of robust chemical sensors for a range of analytes remains an important endeavor for applications such as environmental monitoring, product quality control, and chemical dosimetry. Among the many methods available for chemical sensing, calorimetric techniques remain advantageous in that the human eye can be used for signal transduction, rather than extensive instrumentation.

Though calorimetric sensors currently exist for a range of analytes, most are based upon employing dyes or colored chemical indicators for detection. Such compounds are typically selective, meaning arrays are necessary to enable detection of various classes of compounds. Moreover, many of these systems have lifetime limitation issues, due to photobleaching or undesirable side reactions. Other optical sensing techniques, such as surface plasmon resonance and spectral interferometry, require substantial signal transduction hardware to provide response, and thus are not useful for simple visual indication.

SUMMARY

The present disclosure relates to plasma deposited microporous analyte detection layers, methods of forming analyte detection layers, and analyte sensors including the same are disclosed.

One aspect of the disclosure includes an analyte sensor having a substrate and a microporous amorphous random covalent network layer. The microporous amorphous random covalent network layer includes silicon, carbon, hydrogen and oxygen with a mean pore size in a range from 0.3 to 10 nanometers and an optical thickness in a range from 0.2 to 2 micrometers and a total volume wherein at least 20% of the total volume is pore volume.

Another aspect of the disclosure includes a method of forming an analyte detection layer including the steps of forming a plasma from a gas mixture including an organosilane, oxygen, and a hydrocarbon, then depositing the plasma on a substrate to form an amorphous random covalent network layer, and then heating the amorphous covalent network layer to form a microporous amorphous random covalent network layer.

The above summary is not intended to describe each disclosed embodiment or every implementation of the present disclosure. The Figures, Detailed Description and Examples that follow more particularly exemplify these embodiments.

BRIEF DESCRIPTION OF THE DRAWINGS

The disclosure may be more completely understood in consideration of the following detailed description of various embodiments in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present disclosure provides plasma deposited microporous analyte detection layers, methods of forming analyte detection layers, and analyte sensors including the same are disclosed. These sensors can be formed by plasma deposition of thin films from a gas phase to form an amorphous random covalent network layer. A high degree of porosity is achieved by heating these amorphous random covalent network layers to drive out hydrocarbon and/or hydrogen from the amorphous random covalent network layer. In many embodiments, these analyte detection layers have superior sensing properties to detect organic vapors even at small concentrations.

For the following defined terms, these definitions shall be applied, unless a different definition is given in the claims or elsewhere in this specification.

The term "analyte" means the specific component that is being detected.

The phrase "porous material" or term "porous" means a material containing a continuous network of pores throughout its volume.

The phrase "pore size" means mean pore diameter.

The phrase "microporous material" means a material containing a continuous network of pores throughout its volume, where the pores have a mean dimension in a range from 0.3 to 100 nanometers.

The phrase "substantially continuous" means a layer of material is non-porous, but may have cracks, grain boundaries, or other structures that create pathways through the layer of material. A "substantially continuous" layer may be non-porous, but permeable to one or more analytes.

The term "discontinuous" means a layer of material having at least two separate and distinct islands with empty space therebetween, wherein the at least two separate and distinct islands with empty space therebetween are within a given plane.

The recitation of numerical ranges by endpoints includes all numbers subsumed within that range (e.g. 1 to 5 includes 1, 1.5, 2, 2.75, 3, 3.80, 4, and 5).

As used in this specification and the appended claims, the singular forms "a", "an" and "the" include plural referents unless the content clearly dictates otherwise. Thus, for example, reference to a composition containing "a layer" includes of two or more layers. As used in this specification and the appended claims, the term "or" is generally employed in its sense including "and/or" unless the content clearly dictates otherwise.

Unless otherwise indicated, all numbers expressing quantities of ingredients, measurement of properties and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

Figure 1:
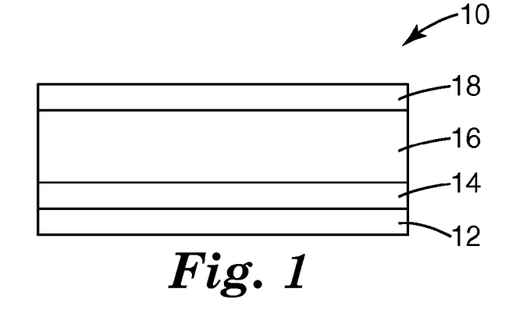
FIG. 1 is a schematic cross-sectional view of an illustrative analyte sensor.

A general depiction of one embodiment of an analyte sensor is illustrated in FIG. 1. The exemplary multi-layered film sensor 10 includes a substrate layer 12, a reflective layer 14, a detection layer 16, and a semi-reflective layer 18. In many embodiments, the sensor films 10 can be used to detect the presence and/or concentration of an analyte or of a mixture of analytes.

The analyte may be a gas (e.g., a vapor) or a liquid, for example. In some embodiments, the analyte is a molecule. The analyte may be present in a gaseous medium (such as, for example, air) or liquid medium (such as, for example, water). In some embodiments, the analyte is an organic molecule or organic material.

In one embodiment, the analyte is detected by a change in the optical thickness of the detection layer 16 upon exposure to the analyte. The analyte passes through an outer semi-reflective layer 18 (if present) and changes the optical thickness of the detection layer 16. In one embodiment the analyte is adsorbed into at least a portion of the detection layer 16. Upon adsorption, color changes (often vivid) of the sensor 10 can indicate the presence of the analyte. In many embodiments, the change in optical thickness is observable in the visible light range and can be detected by the unaided human eye. However, sensors 10 can be designed to show a change in optical thickness when subjected to other light sources or radiation sources such as, for example, ultraviolet (UV), infrared (IR), or near infrared (NIR).

A variety of detection mechanisms can also be used, but this is not required. Examples of suitable detection mechanisms include spectrophotometers, fiber optic spectrophotometers, and photo-detectors, e.g., charge coupled devices (ccd), digital cameras, and the like.

In some embodiments, the sensor 10 includes a substrate 12. The substrate 12 is formed of one or more suitable materials capable of providing support or other functions for the calorimetric sensor 10. The substrate 12 can be flexible or non-flexible. The substrate 12 may be transparent, opaque, or reflective. The substrate 12 can be permeable to the analyte or allow the analyte to diffuse through the substrate 12. The substrate material can be tailored to the application. In many embodiments, it is suitable for use in a vacuum deposition process. In some embodiments, the substrate 12 can block or permit transport of the analyte through the substrate 12. Examples of substrates 12 that permit transport of the analyte through the substrate 12 include woven and non-woven materials and permeable (or perforated or porous) solids, such as the aluminum oxide disk used in Example 5 described below, among others.

In some embodiments, the sensor 10 includes a reflective layer 14. The reflective layer 14 can include any material that can form a fully reflective or semi-reflective layer. In many embodiments, the material is fully (e.g., greater than 90%, 95% or 99%) light reflective at a thickness of about 20 to about 200 nm to a light wavelength of interest. Thinner or discontinuous layers can be used to make the reflective layer 14 semi-reflective. The reflective layer 14 may be made discontinuous by wet etching, reactive ion etching, laser ablation, and the like. In many embodiments, the reflective layer 14 is made to be more reflective than the semi-reflective layer 18 (described below), sometimes it is desirable to have the reflectivity of the reflective layer 14 and semi-reflective layer 18 be the same or similar so a response to the presence of an analyte can be seen from either side of the sensor 10.

A partial listing of suitable materials for the reflective layer 14 include; metals or semi-metals such as aluminum, chromium, gold, nickel, palladium, platinum, titanium, silicon, and silver. Mixtures of metals or metal alloys may also be used, such as gold/palladium or nickel/chromium. Other suitable materials include, for example, metal oxides such as aluminum oxide, chromium oxide, and titanium oxide and nitrides such as silicon nitride, aluminum nitride, titanium nitride, chromium nitride, carbon nitride, and the like.

In some embodiments, the reflective layer 14 is at least 90% reflective, or at least 99% reflective, to a light wavelength of interest. In other embodiments, the reflective layer 14 is a semi-reflective layer, being 20 to 90% reflective, or 30 to 70% reflective, to a light wavelength of interest.

In some embodiments, the reflective layer 14 has a pattern therein wherein first regions of the reflective layer 14 have a greater light reflectance than second regions of the reflective layer 14. In these embodiments, the first and second regions on the reflective layer 14 form a pattern or indicia on the upper surface of or within the reflective layer 14. A patterned reflective layer 14 can include a pattern or indicia so as to create colored images, words, or messages upon exposure of the detection layer 16 to an analyte. Such patterns or indicia can provide easily identifiable warnings for a user upon exposure to an analyte.

Any number of methods may be used to alter the permeability of the reflective layer 14 and/or create a pattern on and within the reflective layer 14. Suitable methods include, but are not limited to, spatially controlling the deposition conditions of the reflective layer 14 to vary the thickness or density of the reflective layer 14. For example, a mask can be placed between the deposition source and the substrate 12 such that the thickness of deposited reflective layer 14 varies from a first location to a second location on an upper surface. The differential permeability and/or creation of a pattern on and within the reflective layer 14 can also be produced by post-treatment of the reflective layer 14 with localized energy inputs such as laser treatment to change the microstructure of the reflective layer 14 or to ablate potions of the reflective layer 14. Wet chemical etching or reactive ion etching of the semi-reflective layer 14 done with appropriate masking are other ways to spatially alter the permeability of the reflective layer 14. Laser treatment or etching techniques could be used, for example, to create an array of holes or lines in the reflective layer 14 through which analyte can permeate and interact with the detection layer 16.

Any of the above-mentioned methods may be used to create one or more patterns on the reflective layer 14. The choice of a given pattern or patterns can depend on a number of factors including, but not limited to, the analyte or analytes of interest, the semi-reflective material or materials used, the message, if any, displayed to a user, or a combination thereof.

In a further exemplary embodiment, the reflective layer 14 is a discontinuous layer. In this embodiment, the composition of the reflective layer 14 may be substantially consistent across the reflective layer 14; however, areas separate the reflective layer 14 into two or more discontinuous regions. The discontinuous semi-reflective layer 14 can be any pattern of semi-reflective islands within a "sea" of exposed areas (i.e., the detection layer 16 is exposed). The size and density of semi-reflective islands on the detection layer 16 can vary as desired, and can be uniformly dispersed or non-uniformly dispersed over an upper surface of the detection layer 16. In some embodiments, the semi-reflective islands can be uniformly dispersed over an upper surface of the detection layer 16 and have at least one dimension (i.e., length, width, or diameter) of at least 1 micrometer, or from 10 to 100 micrometers; however, any semi-reflective island size, shape, and density can be used. In some embodiments, the exposed areas of the detection layer 16 can have at least one dimension (i.e., length, width, or diameter) ranging from 1 to 100 micrometers; however, the exposed areas may have any dimension.

One suitable method for providing a discontinuous reflective layer 14 over a detection layer 16 includes laser ablation. Portions of the semi-reflective layer 14 may be removed by exposing the portions to a laser as described in U.S. Pat. Nos. 6,180,318 and 6,396,616, the subject of which is hereby incorporated in its entirety to the extent it does not conflict with the present disclosure. Another exemplary method that could be used to produce a discontinuous semi-reflective layer 14 is a photo-imaging method, for example.

In some embodiments, the reflective layer 14 also acts as the substrate, providing support for the sensor 10. The reflective layer 14 may also contain holes or be patterned as described above. In some embodiments, the reflective layer 14 includes one or more reflective layers 14. In many embodiments, the reflective layer 14 includes only one reflective layer 14.

The detection layer 16 includes an amorphous random covalent network of atoms. In many embodiments, the detection layer 16 includes an amorphous random covalent network of atoms whose optical thickness changes upon exposure to an analyte. The change in optical thickness can be caused by a dimensional change such as a change in physical thickness of the detection layer 16 or a change in refractive index of the detection layer. The detection layer 16 may change from one color to another, from a color to no color (e.g., silver), or from no color (e.g., silver) to a color, as desired. In some embodiments, the transition in appearance can be from/to a reflective, metallic or silvery appearance.

The detection layer 16 can be porous. In other words, the detection layer 16 can contain a continuous network of pores throughout its volume. The detection layer 16 can have any useful mean pore size such as, for example, 0.3 to 20 nanometers, 0.3 to 10 nanometers, or from 0.5 to 5 nanometers. In many embodiments, the mean pore size can be selected based on the analyte to be detected, since the analyte can fill the pores and alter the physical properties of the detection layer 16.

The detection layer 16 can have any useful pore volume. In many embodiments, the detection layer 16 has a pore volume of at least 0.1 cc/g, or at least 0.3 cc/g, or at least 0.5 cc/g. In many embodiments, at least 20% of the volume of the detection layer 16 is pore volume, or at least 30% of the volume of the detection layer 16 is pore volume, or at least 40% of the volume of the detection layer 16 is pore volume. Throughout the present application the term "microporous'" is intended to broadly encompass materials which may also be described as "nanoporous".

The detection layer 16 can be formed via plasma deposition. Plasma deposition forms an amorphous random covalent network of atoms in a substantially uniform layer. In many embodiments, the amorphous random covalent network thin film is deposited from a plasma including a mixture of silicon, carbon, oxygen and hydrogen atoms or molecules. This amorphous covalent network thin film is then subjected to thermal treatment to heat and drive out hydrocarbons and/or hydrogen to form a microporous analyte detection layer 16. In some embodiments, the plasma is fed with a mixture of organosilane, oxygen, and hydrocarbon to produce an amorphous a-Si:C:H:O thin film, and then is heated to produce a microporous analyte detection layer 16.

Examples of organosilanes include, but are not limited to tetramethylsilane, methylsilane, dimethylsilane, trimethylsilane, ethylsilane, tetraethylorthosilicate (TEOS), tetramethylcyclotetrasiloxane (TMCTS), disilanomethane, bis(methylsilano)methane, 1,2-disilanoethane, 1,2-bis(methylsilano)ethane, 2,2-disilanopropane, diethylsilane, diethylmethylsilane, propylsilane, vinylmethylsilane, divinyldimethylsilane, 1,1,2,2-tetramethyldisilane, hexamethyldisilane, 1,1,2,2,3,3-hexamethyltrisilane, 1,1,2,3,3-pentamethyltrisilane, dimethyldisilanoethane, dimethyldisilanopropane, tetramethyldisilanoethane, tetramethyldisilanopropane, and the like.

Examples of hydrocarbons include, but are not limited straight or branched chain alkanes, alkenes, alkynes, and cyclic hydrocarbons having two to ten carbon atoms. Suitable hydrocarbons include $(C_1-C_{10})$alkanes or $(C_1-C_{10})$alkynes, such as for example, methane, ethane, propane, butane, benzene, cyclohexane, toluene, ethylene, propylene, acetylene, and butadiene.

Any suitable plasma reactor can be utilized to form the amorphous covalent network thin film described herein. One suitable plasma reactor apparatus provides a reaction chamber having a capacitively-coupled system with at least one electrode powered by an RF source and at least one grounded electrode. One suitable reaction chamber is evacuable and is capable of maintaining conditions that produce plasma treatment. That is, the chamber provides an environment which allows for the control of, among other things, pressure, the flow of various inert and reactive gases, voltage supplied to the powered electrode, strength of the electric field across the ion sheath, formation of a plasma containing reactive species, intensity of ion bombardment, and rate of deposition of the amorphous covalent network film from the reactive species. In one apparatus, aluminum is the chamber material because it has a low sputter yield, which means that very little contamination occurs from the chamber surfaces. However, other suitable materials, such as graphite, copper, glass or stainless steel, may be used. The electrode system may be symmetric or asymmetric. In some plasma apparatus, electrode surface area ratios between grounded and powered electrodes for an asymmetric system are from 2:1 to 4:1, or from 3:1 to 4:1. The powered electrode may be cooled, e.g., with water.

Plasma, created from the gas within the chamber, is generated and sustained by supplying power (for example, from an RF generator operating at a frequency in the range of 0.001 to 100 MHz) to at least one electrode. The RF power source provides power at a typical frequency in the range of 0.01 to 50 MHz, or 13.56 MHz or any whole number (e.g., 1, 2, or 3) multiple thereof. The RF power source can be an RF generator such as a 13.56 MHz oscillator. To obtain efficient power coupling (i.e., wherein the reflected power is a small fraction of the incident power), the power source may be connected to the electrode via a network that acts to match the impedance of the power supply with that of the transmission line (which is usually 50 ohms reactive) so as to effectively transmit RF power through a coaxial transmission line. One type of matching network, which includes two variable capacitors and an inductor, is available as Model # AMN 3000 from RF Power Products, Kresson, N.J. Traditional methods of power coupling involve the use of a blocking capacitor in the impedance matching network between the powered electrode and the power supply. This blocking capacitor prevents the DC bias voltage from being shunted out to the rest of the electrical circuitry. On the contrary, the DC bias voltage is shunted out in a grounded electrode. While the acceptable frequency range from the RF power source may be high enough to form a large negative DC self bias on the smaller electrode, it should not be so high that it creates standing waves in the resulting plasma, which is inefficient for plasma treatment.

The amorphous covalent network film to be formed in, or passed through, the evacuable chamber. In some embodiments, a multiplicity of amorphous covalent network films may be simultaneously formed by the plasma during the process. For discrete planar articles, plasma deposition can be achieved, for example, by placing the articles in direct contact with the smaller electrode of an asymmetric configuration. This allows the article to act as an electrode due to capacitive coupling between the powered electrode and the article.

Selection of the heating conditions of the plasma deposited amorphous random covalent network thin film allows for the tailoring of the resulting microporous analyte detection layer 16. For example, the resulting microporous analyte detection layer 16 can be either hydrophobic or hydrophilic, depending on the selected heating conditions. In some embodiments, a hydrophobic microporous analyte detection layer 16 can be formed by heating the plasma deposited amorphous random covalent network thin film in an inert (or reducing) atmosphere and/or at a pressure less than atmospheric. In other embodiments, a hydrophilic microporous analyte detection layer 16 can be formed by heating the plasma deposited amorphous covalent network thin film in an oxidizing atmosphere such as air, oxygen or steam, and at an atmospheric or greater pressure.

The detection layer 16 may include one or more sub-layers. One or more of these sub-layers may be discontinuous or patterned. In some embodiments, the sub-layers can include different materials or be formed with different processing conditions and adsorb different analytes and/or may have different degrees of sensitivity to one or more analytes. The sub-layers may have a variety of configurations. For example, the sub-layers may be stacked to form a stack of two or more layers or may be positioned within the same layer in a side-by-side configuration, as desired. In some embodiments, at least one sublayer may include an inorganic material such as, for example, transparent and metal oxides, nitrides, and oxynitrides of appropriate thickness for producing color by optical interference. Specific examples of suitable inorganic materials include, silicon oxides, silicon nitrides, silicon oxynitrides, aluminum oxides, titanium oxides, titanium nitride, titanium oxynitride, tin oxides, zirconium oxides, and combinations thereof. Other inorganic materials, such as zeolites, are also suitable for use in sublayer(s). Optional sublayer(s) may be microporous, porous, or nonporous. In other embodiments, at least one sublayer may comprise a porous organic polymer. Many intrinsically microporous polymers are known. For example, in *Chemical Communications,* 2004, pp. 230-231, Budd et al. report a series of intrinsically microporous materials containing dibenzodioxane linkages between rigid and/or contorted monomeric building blocks. Further suitable intrinsically microporous polymers are known in the art, for example, as reported by Budd et al. in *journal of Materials Chemistry,* 2005, Vol. 15, pp. 1977-1986 and by McKeown et al. in *Chemistry, A European Journal,* 2005, Vol. 11, 2610-2620, and in PCT Published Application WO 2005/012397 A2 (McKeown et al.).

In many embodiments, the detection layer 16 includes a pattern or indicia so as to create colored images, words, or messages upon exposure to an analyte. In some embodiments, the layer or sublayer is patterned by having one or more portions that are reactive to a particular analyte and one or more portions that are non-reactive to the same analyte. In other embodiments, a pattern of reactive material may be deposited on or formed within a larger non-reactive sublayer. If formed on a non-reactive sublayer, it is preferable to make the patterned layer very thin so that no difference in optical thickness is apparent until an analyte is adsorbed. The patterning can provide easily identifiable warnings for a user upon exposure to an analyte.

Suitable methods of patterning the detection layer 16 include, but are not limited to, spatially controlling the deposition conditions of the detection layer 16 to vary the thickness or density of the detection layer 16. For example, a mask can be placed between the deposition source and the substrate such that the thickness of deposited detection layer 16 varies from a first location to a second location on an upper surface. The differential permeability and/or creation of a pattern on or within the detection layer 16 can also be produced by post-treatment of the detection layer 16 with localized energy inputs such as laser treatment to change the microstructure of the detection layer 16.

For many applications, it is desirable that the detection layer 16 be hydrophobic. This will reduce the chance that water vapor (or liquid water) will cause a change in optical thickness of the detection layer 16 and interfere with the detection of an analyte, for example, in the detection of organic solvent vapors.

The detection layer 16 can have any desired overall thickness. In many embodiments, the detection layer 16 has an overall thickness of more than about 50 nanometers, such as in the range of about 100 to about 1000 nanometers or from 200 to 2000 nanometers. In one embodiment, the detection layer 16 has a layer thickness that is substantially the same throughout the detection layer 16.

In many embodiments, a semi-reflective layer 18 is disposed over the detection layer 16. The semi-reflective layer 18 can include any material that can form a permeable, semi-reflective layer and has a different index of refraction than the detection layer. In many embodiments, the material is semi-reflective at a thickness in a range from 5 to 10 nanometers because at this thickness most analytes will be able to permeate through this layer to the detection layer 16. Desired thicknesses will depend on the material used to form this layer 18, the analyte to be detected, and the medium that will carry the analyte.

Suitable semi-reflection layer 18 materials include, for example, metals and semi-metals such as aluminum, chromium, gold, nickel, palladium, platinum, titanium, silicon, and silver. Mixtures of metals or metal alloys, such as gold/palladium or nickel/chromium may also be used. Other suitable materials that may be included in the semi-reflective layer include oxides such as aluminum oxide, titanium oxide, and chromium oxide, and nitrides such as silicon nitride, aluminum nitride, titanium nitride, chromium nitride and the like.

The semi-reflective layer 18 may be a substantially continuous layer or a discontinuous layer. The semi-reflective layer 18 can include one or more semi-reflective layers. In some embodiments, the semi-reflective layer 18 is a single semi-reflective layer, which is either substantially continuous or discontinuous.

In one exemplary embodiment, the semi-reflective layer 18 is a substantially continuous layer. In this embodiment, the construction and composition of the semi-reflective layer 18 may be substantially consistent across an upper surface of and throughout the semi-reflective layer 18. Alternatively, the construction and/or composition of the semi-reflective layer 18 may vary across an upper surface of and throughout the semi-reflective layer 18. For example, the semi-reflective layer 18 may have a differential permeability such that the semi-reflective layer 18 has higher analyte permeability for a given analyte at a first location on an upper surface of the semi-reflective layer 18 and lower analyte permeability for the same analyte at a second location on the upper surface. The first and second locations on the upper surface of the semi-reflective layer 18 may be randomly positioned relative to one another, or may form a pattern or indicia on the upper surface.

The substantially continuous semi-reflective layer 18 may also have a pattern therein wherein first regions of the semi-reflective layer 18 have a greater light reflectance than second regions of the semi-reflective layer 18. The first and second regions on the semi-reflective layer 18 may form a pattern or indicia on the upper surface of or within the semi-reflective layer 18. Like the patterned detection layer 16 described above, a patterned semi-reflective layer 18 may include a pattern or indicia so as to create colored images, words, or messages upon exposure of the underlying detection layer 16 to an analyte. The semi-reflective layer 18 can provide easily identifiable warnings for a user upon exposure to an analyte.

Any number of methods may be used to alter the permeability of the semi-reflective layer 18 and/or create a pattern on and within the semi-reflective layer 18. Suitable methods include, but are not limited to, spatially controlling the deposition conditions of the semi-reflective layer 18 to vary the thickness or density of the semi-reflective layer 18. For example, a mask can be placed between the deposition source and the substrate such that the thickness of deposited semi-reflective layer 18 varies from a first location to a second location on an upper surface. The differential permeability and/or creation of a pattern on and within the semi-reflective layer 18 can also be produced by post-treatment of the semi-reflective layer 18 with localized energy inputs such as laser treatment to change the microstructure of or to ablate sections of the semi-reflective layer 18. Wet chemical etching or reactive ion etching of the semi-reflective layer 18 done with appropriate masking are other ways to spatially alter the permeability of the semi-reflective layer 18. Laser treatment or etching techniques could be used, for example, to create an array of holes or lines in the semi-reflective layer 18 through which analyte can permeate and interact with the detection layer 16. Any of the above-mentioned methods may be used to create one or more patterns on the semi-reflective layer 18. The choice of a given pattern or patterns can depend on a number of factors including, but not limited to, the analyte or analytes of interest, the semi-reflective material or materials used, the message, if any, displayed to a user, or a combination thereof.

In a further exemplary embodiment, the semi-reflective layer 18 is a discontinuous layer. In this embodiment, the composition of the semi-reflective layer 18 may be substantially consistent across the semi-reflective layer 18; however, areas separate the semi-reflective layer 18 into two or more discontinuous regions. The discontinuous semi-reflective layer 18 may comprise any pattern of semi-reflective islands within a "sea" of exposed areas (i.e., the detection layer 16 is exposed). The size and density of semi-reflective islands on the detection layer 16 may vary as desired, and may be uniformly dispersed or non-uniformly dispersed over an upper surface of the detection layer 16. The semi-reflective islands can be uniformly dispersed over an upper surface of the detection layer 16 and have at least one dimension (i.e., length, width, or diameter) of at least 5 nm, or from 10 to 1000 nm; or from 1 to 10 micrometers; however, any semi-reflective island size, shape, and density may be used. In some embodiments, the exposed areas of the detection layer 16 can have at least one dimension (i.e., length, width, or diameter) ranging from 1 to 100 micrometers; however, the exposed areas may have any dimension.

One suitable method for providing a discontinuous semi-reflective layer 18 over a detection layer 16 includes laser ablation. Portions of the semi-reflective layer 18 may be removed by exposing the portions to a laser as described in U.S. Pat. Nos. 6,180,318 and 6,396,616, the subject of which is hereby incorporated in its entirety to the extent it does not conflict with the present disclosure. Another exemplary method that could be used to produce a discontinuous semi-reflective layer 18 is a photo-imaging method, for example.

In one embodiment, the discontinuous semi-reflective layer 18 includes a number of semi-reflective islands uniformly dispersed over an upper surface of the detection layer 16, where each semi-reflective island has an upper surface area in the shape of a square or circle having a length, width, or diameter of at least 1 micrometer, or from 10 to 100 micrometers. It should be understood that each semi-reflective island may have an upper surface area in a variety of shapes including, but not limited to, triangular, rectangular, star-shaped, diamond-shaped, etc., and one or more dimensions of at least 1 micrometer, or from 10 to 100 micrometers. Further, it should be understood that each semi-reflective island can be either permeable or impermeable to one or more analytes. When the semi-reflective islands are permeable to one or more analytes, the calorimetric sensor allows one or more analytes to contact the detection layer 16 directly through exposed areas, as well as indirectly through the semi-reflective islands.

The disclosed detection layer 16 or sensor 10 may be used alone or may be part of a device for detecting the presence and/or concentration of one or more analytes. In one embodiment, the detection layer 16 or sensor 10 is at least partially enclosed by a housing. The housing can include at least one opening positioned above the semi-reflective layer 18 or detection layer 16 so that the semi-reflective layer 18 or detection layer 16 is viewable through the at least one opening. In some embodiments, the housing includes at least one opening, wherein the opening provides a restricted view of an upper surface of the semi-reflective layer 18 or detection layer 16 so as to minimize any potential change in the viewable color of the sensor (and confusion of the user as to the sensor reading) due to the angle of view. In some embodiments, the restricted view allows a view of the upper surface of the semi-reflective layer 18 or detection layer 16 within an angle of ±30 degrees or ±15 degrees from a normal view (i.e., a view from a position perpendicular to the outer surface of the semi-reflective layer 18 or detection layer 16).

The sensors 10 described herein can be used in a system including the sensor 10, a light source, and, optionally, a means of (a device for) monitoring the sensor 10 for a change of color. The light source can be a natural and/or artificial light source. The monitoring can be done in a variety of ways. It could be done visually, with a photo-detector, or by other suitable means.

The analyte to be detected by the detection layer 16 may be present in a vapor or liquid medium. For example, an analyte may be present in the atmosphere or in a liquid solvent. In either case, in many embodiments, at least a portion of the analyte permeates through the semi-reflective layer 18 (if present) of the sensor 10 to interact with the detection layer 16.

Two or more sensors 10 may be used together to form an array. The array may be in any suitable configuration. For example, an array may include two or more sensors 10 side by side, or the sensors 10 can be attached to, or constructed on, opposite sides of a substrate. The sensors 10 within a given array may be of the same type or may be different. Arrays of sensors 10 would be useful for identification of analytes, based upon their unique response signatures from the array in aggregate, as opposed to only detecting the presence of a chemical agent.

The sensors 10 can have many useful applications, e.g., to detect a wide range of organic vapors, for example. The sensors 10 may be used to detect the presence and/or concentration of a given analyte within a solution or gas. Sensor arrays may be used to detect the presence and/or concentration of one or more analytes within a solution or gas.

In many embodiments, prior to use, the multi-layered film sensors of the present invention are substantially free of an analyte to be detected. The "unexposed" sensor 10 prior to use can displays a first color or be colorless (silver) when viewed through the semi-reflective layer 18 (if present). Upon exposure to one or more analytes to be detected, the "unexposed" sensor 10 converts to an analyte-containing calorimetric sensor. The analyte-containing calorimetric sensor either (i) displays a second color that is different from the first color, or (ii) undergoes a color change from a first color to a silver (or colorless) condition.

The plasma enabled microporous analyte detection films described herein have one or more of the following desirable characteristics: controlled composition by choice of gas phase chemistry; a high degree of porosity; a large change in optical thickness upon heating; can be either hydrophilic and hydrophobic depending upon the heating conditions; and/or a large refractive index (1.9) of the skeleton. These plasma deposition processes are simple and robust and have one or more of the following advantages: a dry, clean method of synthesis without the use of toxic compounds; a synthesis of uniform films of consistent color; are easily amenable for continuous, single pass processing; have the ability to spatially modulate the optical properties by heating with laser radiation or other means of patterned heating; and/or plasma treatment in gases such as $H_2$, $CH_4$, $CF_4$, $O_2$ to render hydrophilicity, hydrophobicity, oleophilicity, oleophobicity, etc., after the heating step. Analyte sensors described herein have dramatically improved combination of sensor characteristics including one or more of the following: hydrophobicity of the analyte detection layer; simple construction requiring a single dielectric or porous layer as opposed to multiple dielectric or porous layers (the single layer construction demonstrates that a single layer construction can provide good sensitivity for detection of organic vapors); fast response time; fast rise in response at low concentrations; and/or excellent response to organic vapors under humid conditions.

The present invention should not be considered limited to the particular examples described herein, but rather should be understood to cover all aspects of the invention as fairly set out in the attached claims. Various modifications, equivalent processes, as well as numerous structures to which the present invention can be applicable will be readily apparent to those of skill in the art to which the present invention is directed upon review of the instant specification.

EXAMPLES

Test Methods

Optical thickness was measured by normal incidence reflectometry using a spectrometer (USB-2000 from Ocean Optics, Dunedin, Fla.) and a bifurcated optical fiber bundle. White light from a tungsten halogen source (model LS-1 from Ocean Optics, Dunedin, Fla.) was introduced at normal incidence using one of the legs of the bifurcated cable and the reflection probe was placed in close proximity (a few millimeters) to the substrate surface. The reflected light intensity was monitored by the spectrometer. The peak locations of the reflected extrema were used to calculate the optical thickness according to the procedure explained in a research publication (S. V. Babu, Moses David and Ramesh C. Patel, Applied Optics (30) 1991 pp 839-846).

Plasma Reactor

The plasma deposited amorphous random covalent network layers were deposited in a planar RF plasma system. The system was pumped by a turbomolecular pump (Balzers, Model TPH2000) backed by dry pumping station (Edwards roots pump EH1200 and a iQDP80 dry mechanical pump). The gas flow rates were controlled by MKS digital flow controllers. RF power was delivered at a frequency of 13.56 Mhz from a 3 kW RFPP power supply (Advanced Energy Model RF30H) through a matching network. The base pressure in the chamber prior to deposition of the amorphous covalent network layers was 1E-3 Pa. Substrate samples were taped to the electrode with kapton tape.

Example 1

Deposition of Plasma Layer from TMS/Butadiene/O2 Mixture

Silicon substrate samples were taped onto the powered electrode and the substrate was primed with 400 sccm of argon gas at a pressure of 8 mTorr and RF power of 1000 watts for 45 seconds. The DC self-bias on the substrate during the argon priming step was −860 volts. Immediately after the priming step, a gas mixture containing tetramethysilane, 1,3 butadiene and oxygen were fed into the vacuum chamber. Plasma was maintained under the conditions described below, producing a 1.061 micrometer amorphous random covalent network film:

Flow rate of tetramethysilane: 100 sccm
Flow rate of 1,3-butadiene: 160 sccm
Flow rate of oxygen: 100 sccm
Process pressure: 35 mTorr
Rf power: 100 Watts
DC Self Bias Voltage: −120 Volts
Deposition time: 16.5 minutes.

Example 2

Synthesis of Microporous Amorphous Covalent Network Layer

The amorphous covalent network film produced in Example 1 above was subjected to different types of heating conditions to produce the microporous analyte detection films. The different heating conditions are summarized in Table 1 below:

TABLE 1

| Sample No. | Ambient | Heating Temp, C. | Heating Time, min | Optical Thickness, nm | Optical Thickness Change |
|---|---|---|---|---|---|
| Control |  | None | 0 | 1550 |  |
| 1 | Air | 450 | 2 | 1450 | −6.7 |
| 2 | Air | 450 | 5 | 1260 | −19 |
| 3 | Air | 450 | 30 | 1110 | −28 |
| 4 | Air | 450 | 60 | 1080 | −31 |
| 5 | Air | 450 | 1440 | 860 | −44 |

TABLE 1-continued

| Sample No. | Ambient | Heating Temp, C. | Heating Time, min | Optical Thickness, nm | Optical Thickness Change |
|---|---|---|---|---|---|
| 6 | Vacuum | 500 | 60 | 1440 | −6.8 |
| 7 | Nitrogen | 500 | 60 | 1340 | −10 |
| 8 | Air | 450 | 1440 | 921 | −38 |
| 9 | Nitrogen | 550 | 1440 | 1235 | −21 |

From the above table, it appears that the detection layer optical thickness change gradually increases with the amount of heating time and this change can be quite large (44% change for prolonged heating in air ambient at 450 degrees centigrade for 1440 minutes). For comparable heating times, nitrogen or vacuum heating appears to produces a smaller change in the detection layer optical thickness.

Example 3

Reflectance Spectra of Microporous Layer

This example demonstrates how the peak positions of the reflectance oscillations caused by thin film interference effects are shifted by the heating process exemplifying the differences in the heating behavior of the air, vacuum and nitrogen heated films.

Figure 2A:
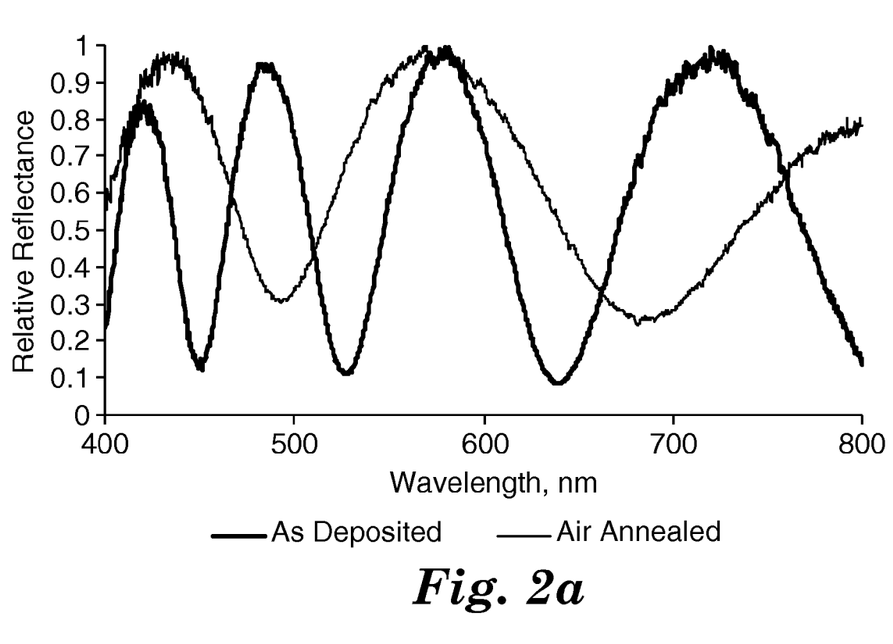
FIGS. 2 to 6 are graphs of the data measured in Examples 3 to 9.
Figure 2B:
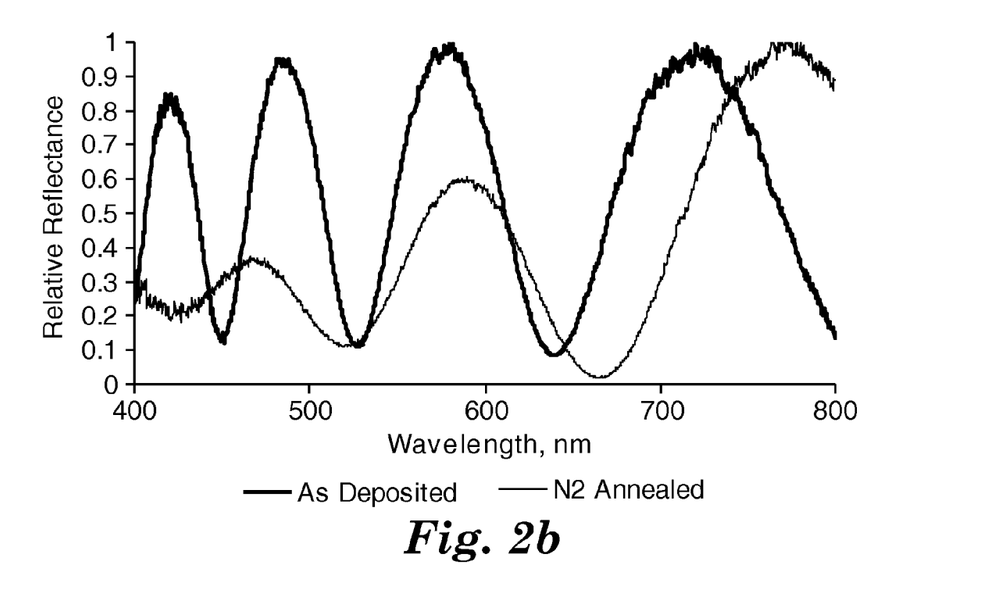
Figure 2C:
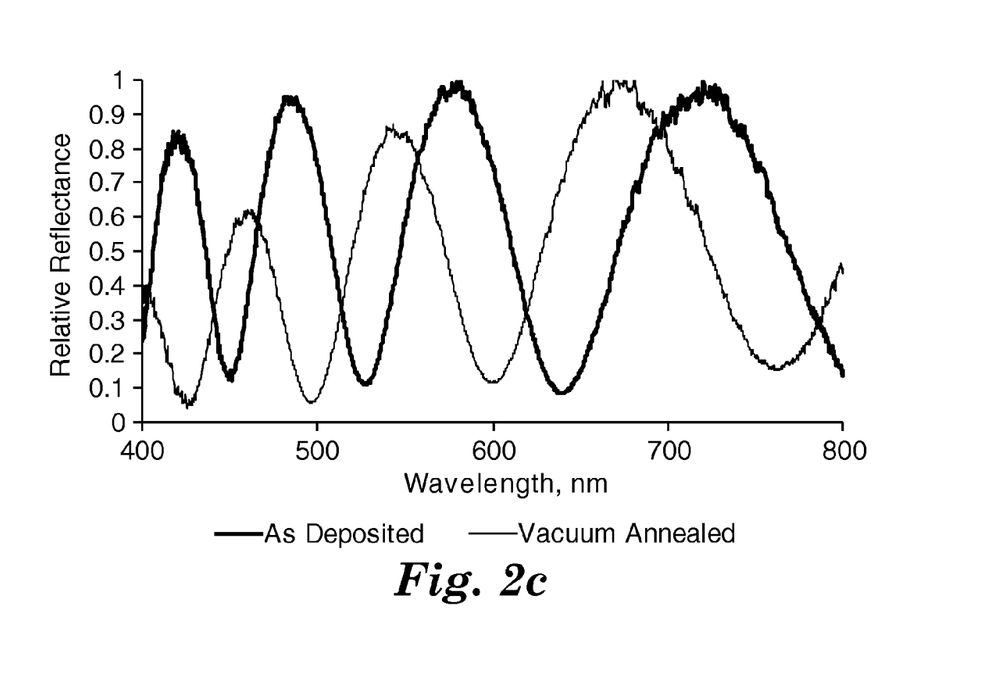

The reflectance of the amorphous covalent network layer produced in Example 1 above was measured before and after heating and the results are shown in FIG. 2 for heating in air and nitrogen respectively.

From FIG. 2 it appears that a significant shift in the peak positions are seen for all the heated films due to the porosity created in them; the shift in peak positions is greater for the air heated films when compared to the nitrogen and vacuum heated films; and the amplitude of the reflectance oscillation decreases with decreasing wavelength for the vacuum and nitrogen heated films. The amplitude reduction appears to be the most prominent for the nitrogen-heated film. This amplitude reduction appears to imply that the heated films have increasing levels of absorption with decreasing wavelength, going towards the blue and ultraviolet regions of the electromagnetic spectrum.

Example 4

Spectroscopic Ellipsometry of Microporous Layer

This example demonstrates the magnitude of the optical constants and porosity created in the microporous amorphous random covalent network layer due to the heating process. The amorphous random covalent network layer deposited according to Example 1 was heated in air and the resulting microporous amorphous covalent network layer was analyzed using Variable Angle Spectroscopic Ellipsometry (VASE) to determine the porosity and optical constants of the amorphous random covalent network layer before and after heating. The thickness and porosity of the as-deposited film were determined to be 453 nanometers and 0% respectfully, whereas, the thickness and porosity of the air heated amorphous random covalent network layer were determined to be 361 nanometers and 47% respectfully. The refractive index of both layers decreased with a similar curve as light wavelength increased from 350 to 1000 nanometers, however the heated (microporous) amorphous random covalent network layer had a refractive index of about 25% greater than the as-deposited film at each wavelength from 350 to 1000 nanometers.

Example 5

Color Shift of Microporous Layer Upon Exposure to Toluene Vapor

This example demonstrates the ability of the microporous random amorphous covalent network layer on a substrate to detect toluene vapor. The substrate for this example was a porous aluminum oxide disk, which was coated first with an aluminum reflective film. A plasma layer was then deposited on top of the aluminum layer in a manner described in Example 1. The plasma deposited amorphous random covalent network layer was heated in air at 450 degrees centigrade for 30 minutes as in Example 2 to form a nonporous amorphous covalent network layer. After the heating step, a semi-reflective film of aluminum was sputtered onto the microporous amorphous covalent network layer to create an interference color. The reflectance spectrum of this colored sensor article was measured and recorded at different exposure levels of toluene (50, 100, 200, 500, 1000, 2000, 4000 ppm).

The results appear to show how the reflectance of the sensor article at different wavelengths changes as the sensor article is exposed to toluene vapor at different tolune concentrations. From the results, it appears that there is a distinct and quick change in the reflectance even when the concentration is as small as 50 ppm. Furthermore, fast, distinct changes appear to be apparent at every other concentration change at 100, 200, 500, 1000, 2000 and 4000 ppm respectively. These results demonstrate the efficacy of the microporous amorphous covalent network layer system as a means to detect organic vapors, even at low concentrations.

Example 6

MEK Response of Detection Layer to Heating Conditions

This example demonstrates the ability to tailor the sensitivity of the microporous analyte detection layer to heating conditions. Analyte detection films were prepared on silicon substrates and heated under different conditions according to the procedure outlined in Examples 1 and 2. The resulting articles were exposed to methyl ethyl ketone (MEK) vapor under different concentrations and the color shift was measured as a function of the MEK concentration and illustrated in FIG. 3.

Figure 3:
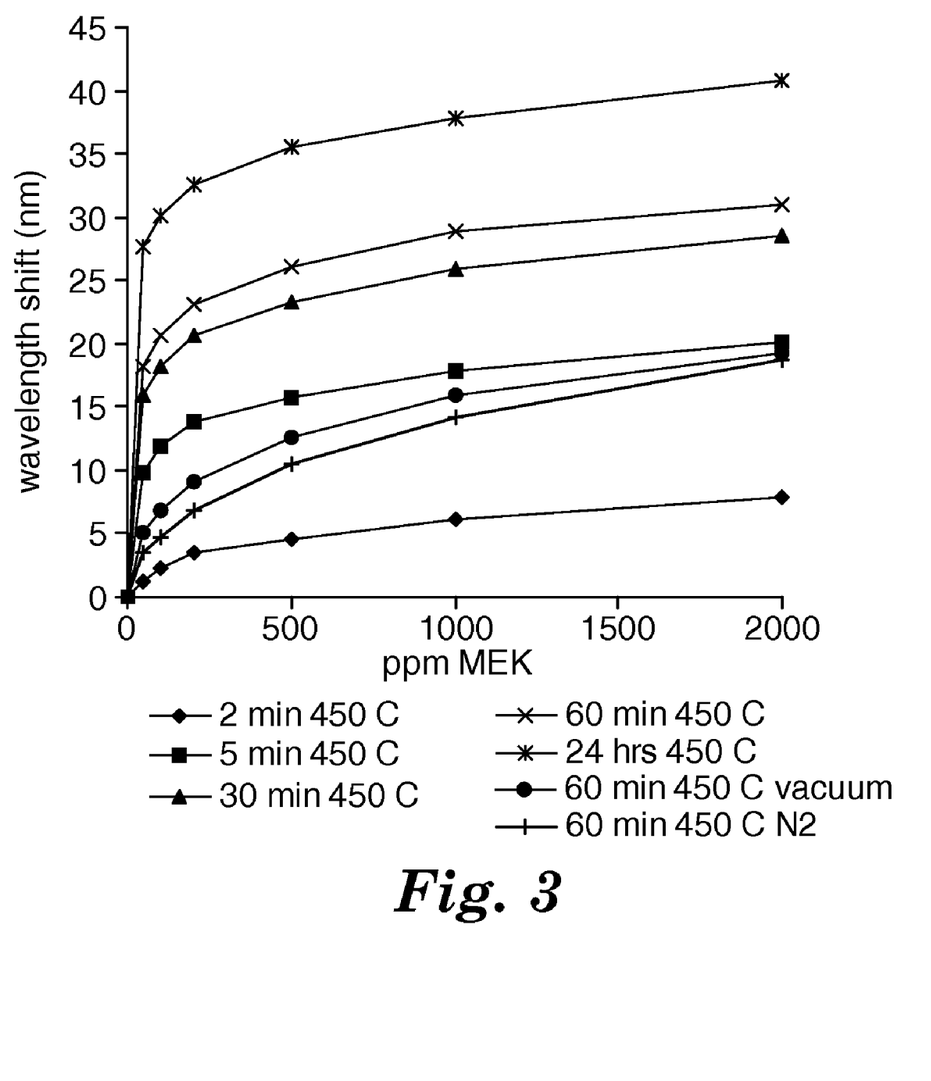

It appears from FIG. 3 that the sensitivity of the detection layer is a strong function of the heating conditions. All of the curves except for those marked as vacuum or N2 heated were heated in an air ambient. For these air heated articles, the sensitivity appears to be a direct function of the heating time. The wavelength shift at a 50 ppm concentration of MEK appears to increase gradually from 1.2 to 27.8 as the heating time is increased from 2 minutes to 24 hours. Furthermore, it appears that the biggest change occurs within the first 50 ppm, indicating a large proportion of very small pores less than 1 nm in size. The vacuum and nitrogen heating response appears moderate for the heat times of 60 minutes attempted in this heating study. The wavelength shift of 27.8 nm for a 50 ppm concentration organic vapor appears very high and can be easily distinguished by the human eye.

Example 7

Toluene Response of Detection Layer to Heating Conditions

This example demonstrates the ability to tailor the sensitivity of the microporous analyte detection layer to heating conditions. Analyte detection films were prepared on silicon substrates and heated under different conditions according to the procedure outlined in Examples 1 and 2. The resulting articles were exposed to toluene vapor under different concentrations and the color shift was measured as a function of the toluene concentration and illustrated in FIG. 4.

Figure 4:
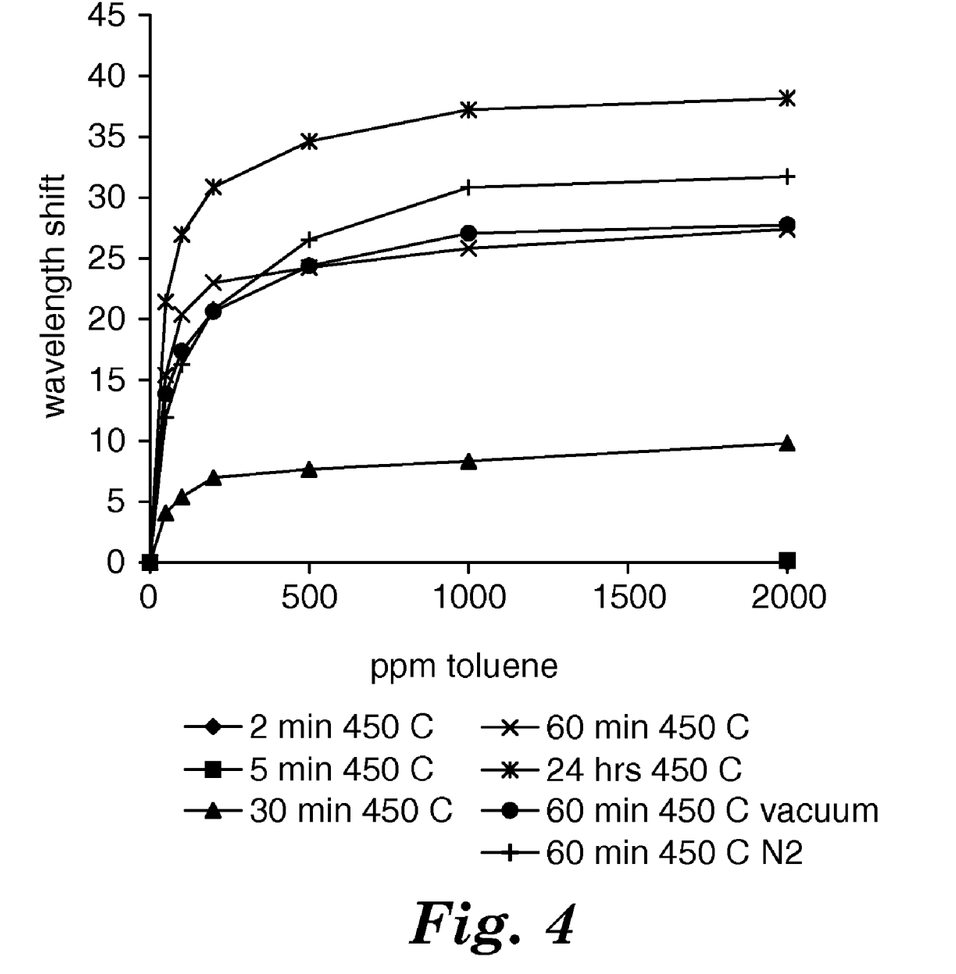

It appears from FIG. 4 that the sensitivity of the detection layer is a strong function of the heating conditions. All of the curves except for those marked as vacuum or nitrogen heated were heated in an air ambient. For these air heated articles, the sensitivity appears to be a direct function of the heating time. The wavelength shift at a 50 ppm concentration of toluene appears to increase gradually from 0 to 21.4 as the heating time is increased from 2 minutes to 24 hours. Furthermore, it appears that the biggest change occurs within the first 50 ppm, indicating a large proportion of very small pores less than 1 nm in size. The vacuum and nitrogen heated articles also show excellent response to toluene vapors.

Example 8a

High Humidity Ethylbenzene Response of Detection Layer to Heating Conditions This example demonstrates the ability to tailor the high humidity sensitivity of the microporous analyte detection layer to heating conditions. Analyte detection films were prepared on silicon substrates and heated under different conditions according to the procedure outlined in Examples 1 and 2. The resulting articles were exposed to ethylbenzene vapor (at 50, 100, 200, 500, 1000, 2000 ppm) under highly humid conditions of 72% relative humidity (RH) and the reflectance spectrum was measured as a function of the ethylbenzene concentration.

The results appear to demonstrate the ability of the analyte detection films to detect ethylbenzene vapors even in the presence of high levels of moisture (up to 72% RH). The results appear to indicate there is negligible shift in the peak locations of the spectra when the analyte detection films are exposed to increasing levels of humidity from 24% RH to to 72% RH, whereas, there is a significant shift when exposed to even 50 ppm of ethylbenzene vapor under these various humid conditions. Furthermore, it appears that the most significant wavelength shift occurs for the smallest concentration of ethylbenzene (50 ppm), indicating that the pore structure of the analyte detection film is suited, with a very small pore size below 1 nm for the detection of organic vapors.

Example 8b

High Humidity Response of Analyte Detection Layer to Heating Conditions

This example demonstrates the ability of the analyte detection layer to detect small concentrations of organic vapors under highly humid conditions and also to tailor the sensitivity of the analyte detection layer by controlling the heating conditions. Analyte detection films were prepared on silicon substrates and heated under different conditions according to the procedure outlined in Examples 1 and 2. The resulting articles were exposed to different levels of ethylbenzene under humid conditions at 72% RH and the color shift was measured as a function of ethylbenzene concentration and illustrated as FIG. 5.

Figure 5:
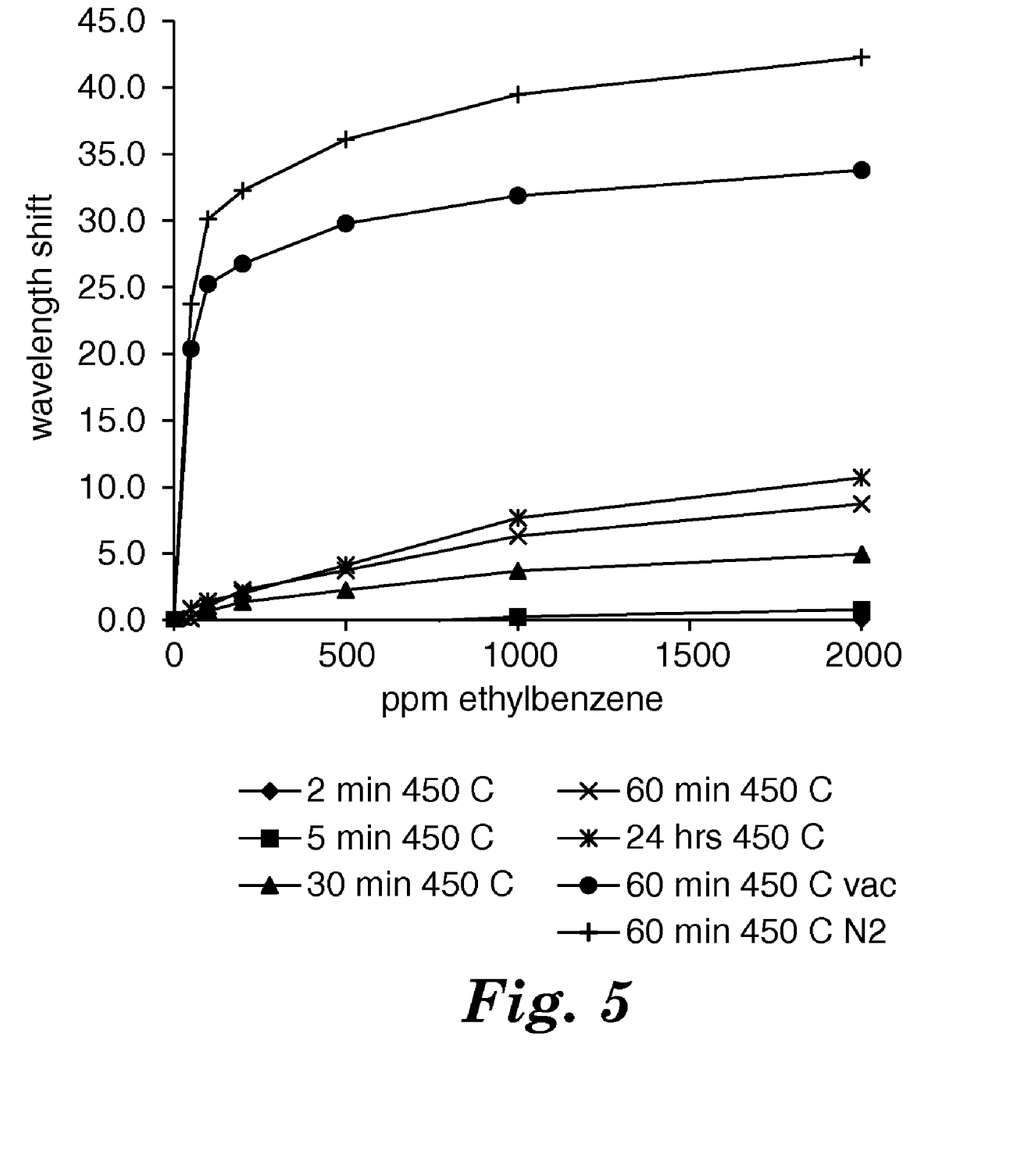

FIG. 5 appears to show significant differences in the response of the analyte detection layer to the heating conditions. All of the analyte detections layers produced by heating in air appear to show a significantly reduced level of sensitivity to ethylbenzene under highly humid conditions. While, analyte detection layers that were heated in nitrogen or vacuum show excellent response to ethylbenzene even at a concentration of 50 ppm under highly humid conditions. The nitrogen and vacuum heated articles appear to show a wavelength shift of 20.4 and 23.8 nm respectively at a concentration of 50 ppm. This result appear to demonstrates the utility of the analyte detection layers as robust layers for the sensing of organic vapors.

Example 8c

Color Simulation of Analyte Detection Layer to Ethylbenzene at 72% RH

This example demonstrates the ability of the analyte detection layer to display a visually perceptive color change when exposed to small concentrations of organic vapor under highly humid conditions. An analyte detection film was prepared on a silicon wafer by heating under nitrogen as described in Examples 1 and 2. The analyte detection layer was then exposed to high humidity and then to increasing concentrations of ethylbenzene. The reflectance spectrum was then measured and recorded.

From the results, it appears that distinct color changes are discerned by the human eye even under small concentrations of organic vapors. These color changes may be further optimized by designing a suitable initial color to effect the most change upon exposure to the organic vapors.

Example 9

High Humidity Response of Analyte Detection Layer to Heating Conditions

Figure 6:
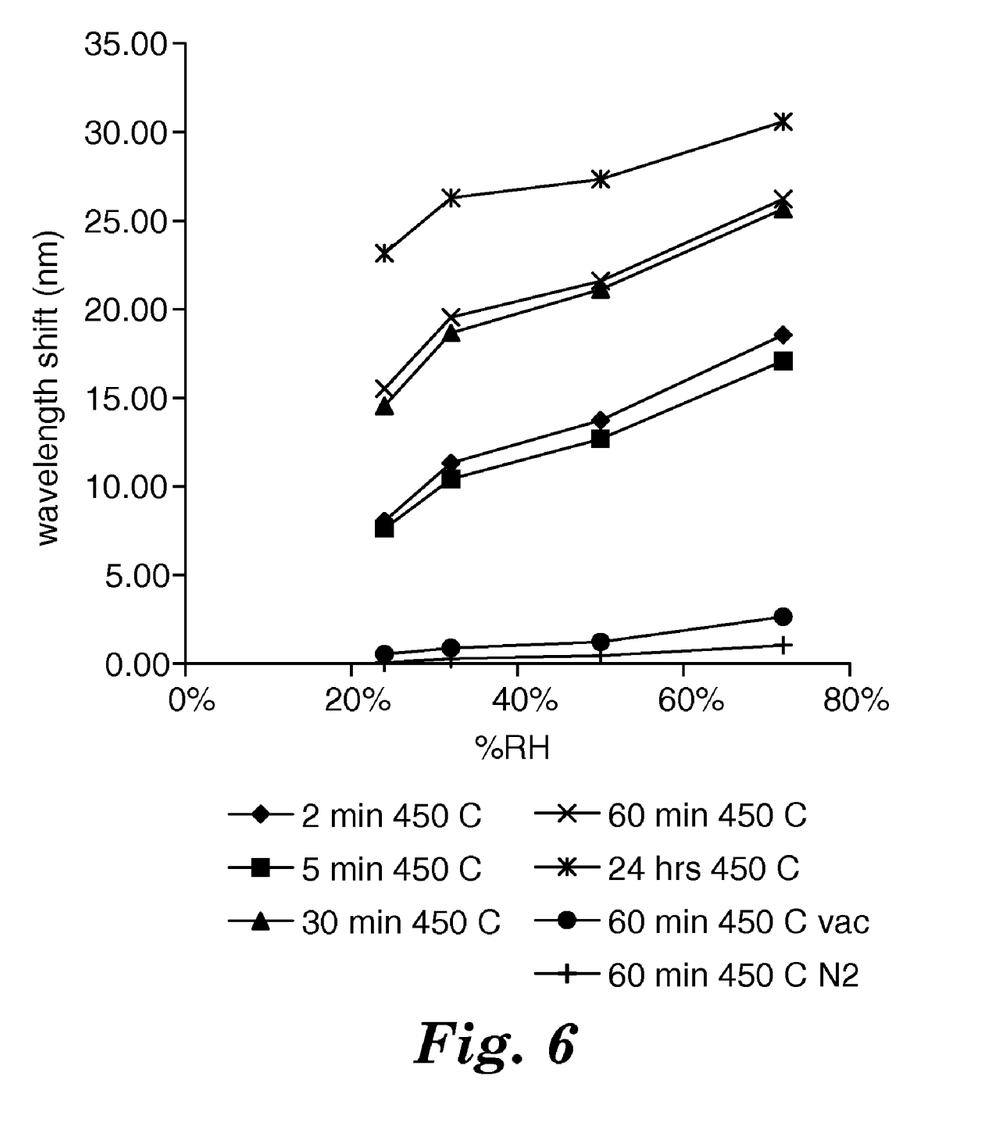

This example demonstrates the ability to tailor the hydrophilicity and hydrophobicity of the analyte detection layer by choice of the heating conditions. Analyte detection films were prepared on silicon substrates and heated under different conditions according to the procedure outlined in Examples 1 and 2. The resulting articles were exposed to different levels of relative humidity in the range of 24% to 72% and the color shift was measured as a function of the percent relative humidity (% RH). The results of these measurements are illustrated in FIG. 6.

All of the air heated articles appear to show significant response to humidity in the range of 20% RH to 72% RH, whereas, the nitrogen and vacuum heated articles appear to show very little response to humidity. Thus, the hydrophilicity or hydrophobicity of the analyte detection articles may be controlled by the choice of the heating conditions for different applications.

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention.

Thus, the scope of the invention should not be limited to the exact details of the compositions and structures described herein, but rather by the language of the claims that follow. The complete disclosures of the patents, patent documents and publications cited herein are incorporated by reference in their entirety as if each were individually incorporated. In case of any conflict, the present specification, including definitions, shall control.

What is claimed is:

1. A method of forming an analyte detection layer comprising:
   forming a plasma from a gas mixture comprising an organosilane, oxygen, and a hydrocarbon;
   depositing the plasma on a substrate to form an amorphous random covalent network layer; and
   heating the amorphous random covalent network layer to form a microporous amorphous random covalent network layer.

2. A method according to claim 1 wherein the heating step comprises heating the amorphous random covalent network layer to form a microporous amorphous random covalent network layer having a mean pore size in a range from 0.5 to 10 nanometers.

3. A method according to claim 1 wherein the depositing step comprises depositing the plasma on a substrate to form an amorphous random covalent network layer having an optical thickness in a range from 0.1 micrometers to 2 micrometers.

4. A method according to claim 1 wherein the forming step comprises forming a plasma from a gas mixture comprising an organosilane, oxygen, and a ($C_1$-$C_{10}$)alkane or a ($C_1$-$C_{10}$) alkyene.

5. A method according to claim 1 wherein the heating step comprises heating the amorphous random covalent network layer in an oxidizing atmosphere to form a hydrophilic microporous amorphous covalent network layer having a mean pore size in a range from 0.5 to 10 nanometers.

6. A method according to claim 1 wherein the heating step comprises heating the amorphous random covalent network layer in a reducing atmosphere to form a hydrophobic microporous random amorphous covalent network layer having a mean pore size in a range from 0.5 to 10 nanometers.

7. A method according to claim 1 wherein the depositing step comprises depositing the plasma on a light reflective substrate to form an amorphous random covalent network layer.

8. A method according to claim 1 wherein the forming step comprises forming a plasma from a gas mixture comprising tetramethylsilane, oxygen, and 1,3-butadiene.

9. A method according to claim 1 further comprising exposing the microporous amorphous random covalent network layer to an analyte to form an exposed microporous amorphous random covalent network layer and detecting the analyte through an optical change in the exposed microporous amorphous random covalent network.

10. A method according to claim 1 wherein the depositing step comprises depositing the plasma on a permeable substrate to form an amorphous random covalent network layer.

11. A method according to claim 1 further comprising disposing a light reflective layer on the microporous amorphous random covalent network layer.

12. A method according to claim 1 further comprising depositing the plasma on the amorphous random covalent network layer to form a second amorphous covalent network layer.

13. A method according to claim 1 further comprising exposing the microporous amorphous random covalent network layer, having a first optical thickness, to an analyte to form an exposed microporous amorphous random covalent network layer having a second optical thickness being different than the first optical thickness and detecting the analyte through a difference in the first optical thickness and the second optical thickness.

14. An analyte sensor comprising:
   a substrate; and
   a microporous amorphous random covalent network layer comprising silicon, carbon, hydrogen and oxygen, the microporous amorphous covalent network layer having a mean pore size in a range from 0.5 to 10 nanometers and an optical thickness in a range from 0.2 to 2 micrometers and a total volume wherein at least 20% of the total volume is pore volume.

15. An analyte sensor according to claim 14 wherein at least 50% of the total volume is pore volume.

16. An analyte sensor according to claim 14 wherein the microporous amorphous random covalent network layer is disposed on a first light reflective layer.

17. An analyte sensor according to claim 14 wherein the microporous amorphous random covalent network layer is plasma deposited on the substrate, the plasma formed from a gas mixture comprising an organosilane, oxygen, and a hydrocarbon, and then heated.

18. An analyte sensor according to claim 14 wherein the microporous amorphous random covalent network layer is hydrophilic.

19. An analyte sensor according to claim 14 wherein the microporous amorphous random covalent network layer is hydrophobic.

20. An analyte sensor according to claim 14 further comprising a second light reflective layer, wherein the microporous amorphous random covalent network layer is disposed between the first light reflective layer and the second light reflective layer.

21. An analyte sensor according to claim 14 wherein the sensor is a calorimetric sensor.

22. An analyte sensor according to claim 14 further comprising a second microporous amorphous random covalent network layer disposed on the microporous amorphous random covalent network layer.

23. An analyte sensor according to claim 14 wherein the substrate is a permeable substrate.

* * * * *

UNITED STATES PATENT AND TRADEMARK OFFICE
CERTIFICATE OF CORRECTION

PATENT NO. : 8,293,340 B2
APPLICATION NO. : 11/275277
DATED : October 23, 2012
INVENTOR(S) : Moses M David et al.

It is certified that error appears in the above-identified patent and that said Letters Patent is hereby corrected as shown below:

Title Page, Column 2, (Other Publications)
Line 16, delete "Porcessed," and insert -- Processed, --, therefor.

Column 1
Line 14, delete "calorimetric" and insert -- colorimetric --, therefor.
Line 17, delete "calorimetric" and insert -- colorimetric --, therefor.

Column 2
Line 49, delete ""an"" and insert -- "an", --, therefor.

Column 3
Line 44, delete "calorimetric" and insert -- colorimetric --, therefor.

Column 7
Line 58, delete "journal" and insert -- Journal --, therefor.

Column 10
Line 27, delete "calorimetric" and insert -- colorimetric --, therefor.

Column 11
Line 19, delete "calorimetric" and insert -- colorimetric --, therefor.
Line 20, delete "calorimetric" and insert -- colorimetric --, therefor.

Column 12
Line 33, delete "tetramethysilane," and insert -- tetramethylsilane, --, therefor.
Line 38, delete "tetramethysilane:" and insert -- tetramethylsilane: --, therefor.

Column 13
Line 15, delete "centrigrade" and insert -- centigrade --, therefor.

Signed and Sealed this
Nineteenth Day of February, 2013

Teresa Stanek Rea
*Acting Director of the United States Patent and Trademark Office*

CERTIFICATE OF CORRECTION (continued)
U.S. Pat. No. 8,293,340 B2

Column 14
Lines 18-19, delete "centrigrade" and insert -- centigrade --, therefor.
Line 29, delete "tolune" and insert -- toluene --, therefor.

Column 15
Line 47, delete "to to" and insert -- to --, therefor.

Column 18
Line 49, in Claim 21, delete "calorimetric" and insert -- colorimetric --, therefor.